United States Patent [19]

Oliver

[11] Patent Number: 4,808,162
[45] Date of Patent: Feb. 28, 1989

[54] GASTROTOMY TUBE STABILIZER

[76] Inventor: Ruth Oliver, 809 Avis Dr., Upper Marlboro, Md. 20772

[21] Appl. No.: 145,307

[22] Filed: Jan. 19, 1988

[51] Int. Cl.⁴ .............................................. A61M 5/32
[52] U.S. Cl. ............................. 604/180; 128/DIG. 26
[58] Field of Search ............... 604/180, 178, 174–177, 604/179, 327; 128/DIG. 26

[56] References Cited

U.S. PATENT DOCUMENTS

| | | | |
|---|---|---|---|
| 3,487,837 | 2/1967 | Petersen | 128/DIG. 26 |
| 4,516,968 | 5/1985 | Marshall et al. | 604/174 |
| 4,517,971 | 5/1985 | Sorbonne | 604/174 X |
| 4,583,972 | 4/1986 | Shishov et al. | 604/174 |
| 4,659,329 | 4/1987 | Annis | 604/180 |
| 4,666,434 | 5/1987 | Kaufman | 128/DIG. 26 |

Primary Examiner—Stephen C. Pellegrino
Attorney, Agent, or Firm—Richard C. Litman

[57] ABSTRACT

A gastrotomy tube stabilizer comprises an upper, dome-shaped shell and a lower, cup-shaped shell. The lower shell remains affixed to the patient's skin and has a central aperture sufficiently large to permit passage of the gastrotomy tube therethrough and to leave the surrounding wound area exposed. The upper shell has a collar extending upwardly therefrom adapted to retain the gastrotomy tube, and is furnished with plural holes for ventilation. The upper and lower shells are furnished with cooperating interlocking means. When the shells are joined, a protective cavity is formed surrounding the wound area and the position of the gastrotomy tube is maintained. The upper shell may be readily disengaged from the lower shell to afford visual inspection of the wound area and access thereto for cleaning and changing of dressings.

4 Claims, 1 Drawing Sheet

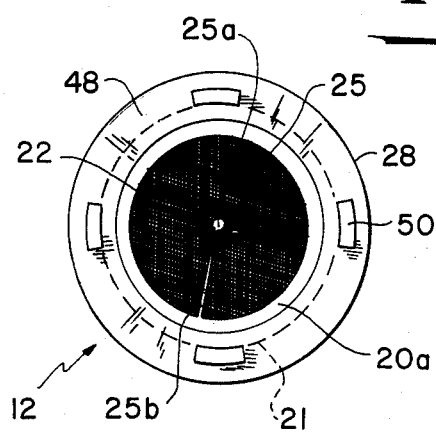
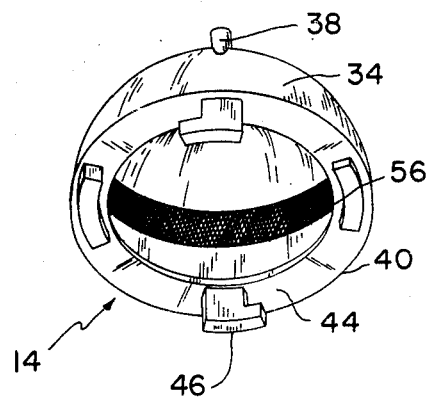
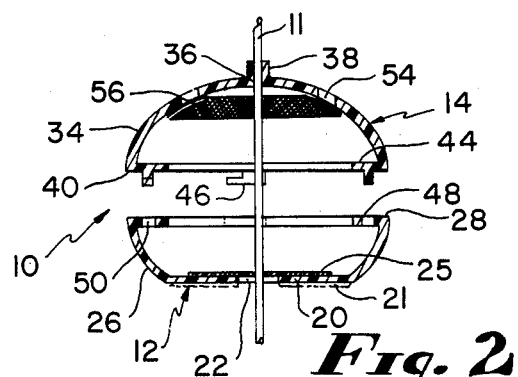
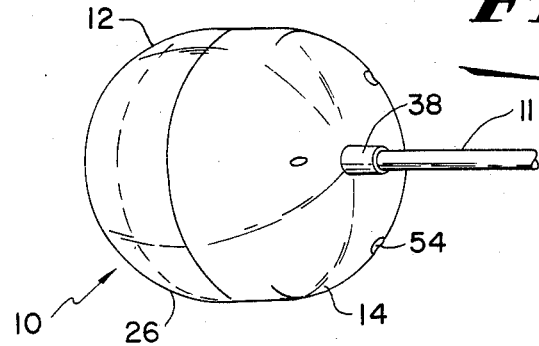

GASTROTOMY TUBE STABILIZER

BACKGROUND OF THE INVENTION

1. Field of the Invention

This invention relates to apparatus for maintaining the position of gastrotomy tubes. More particularly, this invention relates to such apparatus having improved means for ventilating the wound area while protecting it from contaminants and for allowing access to the wound area for cleansing and changing of dressings.

2. Description of the Related Art

Traditionally, gastrotomy tubes and other surgical tubes have been held in place by adhesive tape wrapped around the base of the tube and the adjacent skin surface. Such an arrangement, however, has several disadvantages. First, the tape rubs against the wound area, causing irritation. Second, the wound area is not allowed access to air, a situation that breeds infection. Third, bodily fluids escaping from the wound tend to destroy the adhesive properties of the tape. Fourth, although tape is fairly effective in preventing axial displacement of the tube, it is not effective in preventing rocking or swaying of the tube. Finally, the tape prevents access to the wound area for inspection and cleaning.

Accordingly, several devices have been invented for retaining in place surgical tubes which overcome one or more of the preceding disadvantages. Representative of these are the inventions disclosed in the following patents:

| Patent No. |
| --- |
| 2,898,917 |
| 3,487,837 |
| 4,516,968 |
| 4,633,863 |
| 4,666,433 |

U.S. Pat. No. 2,898,917 to Wallace discloses a retaining device for surgical tubes which comprises a disk removably affixable to the skin and a tube extending upwardly therefrom and which removably retains in position a surgical tube.

U.S. Pat. No. 3,487,837 to Peterson discloses a device for holding catheters in position and having a bell-shaped elastic body resisting axial displacement of the catheter.

U.S. Pat. No. 4,516,968 discloses a catheter shield comprising a dome surrounded by a peripheral, skin engaging flange. Vents may be provided in the shield.

U.S. Pat. No. 4,666,433 to Parks discloses a gastrotomy feeding device having a stabilizer comprising a disk having radial ribs on its underside. The ribs in combination with holes in the disk provide improved ventilation.

All of the above-listed patents disclose devices for holding a surgical tube in place which prevent axial displacement of the tube and/or swaying of the tube. In addition, certain of the above-listed patents, in particular U.S. Pat. Nos. 4,516,986 and 4,666,433, have ventilation holes to allow the wound area to breathe. However, none of the above-listed patents discloses a gastrotomy tube stabilizing device effectively maintaining the position of the tube while providing ready access to the wound area for inspection and cleaning.

SUMMARY OF THE INVENTION

Accordingly, it is an object of the present invention to provide a gastrotomy tube stabilizer comprising a lower shell that remains permanently affixed to the patient's body, and an upper shell which can be readily disconnected from the lower shell to provide access to the wound area for visual inspection and changing of dressings.

It is a further object of the present invention to provide a gastrotomy tube stabilizer which does not contact the wound area and which allows ventilation of the wound area yet protects it from contaminants, thereby protecting the wound area from irritation, decreasing the risk of infection and speeding the process of healing.

It is a basic object of the present invention to provide a gastrotomy tube stabilizer which maintains the position of a gastrotomy tube and protects it from axial displacement and pivoting at the point of entry into the body.

According to the present invention, a gastrotomy tube stabilizer is provided which comprises a lower, cup-shaped shell and an upper, dome-shaped shell. The lower shell has a planar base which is furnished with adhesive means on its underside to enable it to be removably affixed to the patients skin. The base has a central aperture which permits passage of the tube therethrough and which is sufficiently large to leave the wound area exposed. The upper shell terminates at its upper end in an upwardly extending collar which retains the gastrotomy tube. The upper shell can be readily disengaged from the lower shell to provide access to the wound area for visual inspection, cleaning and changing of dressings. When the upper shell is secured to the lower shell, a protective cavity is formed around the wound area to protect if from irritation and infection. Ventilation holes provided in the upper shell allow the wound area to breathe.

BRIEF DESCRIPTION OF THE DRAWINGS

FIG. 1 is a perspective view of the device of the present invention installed on a gastrotomy tube and with the upper shell connected to the lower shell.

FIG. 2 is a cross-sectional view from the side of the device of the present invention installed on a gastrotomy tube and with the upper shell separated from the lower shell.

FIG. 3 is a top plan view of the lower shell of the device of the present invention.

FIG. 4 is a perspective view from below of the upper shell of the device of the present invention.

DETAILED DESCRIPTION OF THE PREFERRED EMBODIMENT

Turning now to the drawings, FIG. 1 shows a gastrotomy tube stabilizer 10 according to the present invention installed on a gastrotomy tube 11 which extends into a patient's stomach through an incision in the abdomen. The stabilizer 10 comprises a lower shell 12 and an upper shell 14. As can be seen more clearly in FIG. 2, lower shell 12 is substantially cup-shaped and has a planar base 20 furnished with a central aperture 22 through which the gastrotomy tube extends and which is sufficiently large to expose the wound area. A disk-shaped gauze pad 25 is placed on the upper surface 20a of planar base 20 to absorb moisture from the wound area. Gauze pad 25 has a central hole 25 permitting passage of the gastrotomy tube therethrough, and a radial slit 25b enabling gauze pad 25 to be changed without removing gastrotomy tube 11. The underside of planar base 20 is furnished with preferably annular adhesive means enabling lower shell 12 to be removably affixed to the patients skin surrounding the wound area. Extending upwardly from edge 21 of planar base 20 is body 26 which terminates in upper rim 28.

Referring again to FIG. 1, upper shell 14 is substantially dome-shaped and has a central opening 36 of substantially the same diameter as the gastrotomy tube. Extending upwardly from central opening 36 is a cylindrical collar 38 whose diameter is also substantially the same as the gastrotomy tube and which is adapted to receive the gastrotomy tube therethrough and maintain it in axial alignment. The body 34 of upper shell 14 extends downwardly from central opening 36 and terminates in lower rim 40, which has the same diameter as upper rim 28 of lower shell 12.

Upper rim 28 of lower shell 12 and lower rim 40 of upper shell 14 are furnished with cooperating means enabling upper shell 14 to be releasably joined to lower shell 12 to form a protective cavity surrounding the wound area. In a preferred embodiment, as shown most clearly in FIGS. 3 and 4, upper shell 14 is furnished with an annular shelf 44 extending inwardly from lower rim 40. Projecting downwardly from annular shelf 44 and inset from lower rim 40 are plural L-shaped teeth 46. Upper rim 28 of lower shell 12 is also furnished with an inwardly extending ledge 48 which is furnished with plural inset slots 50. When L-shaped teeth 46 are inserted into slots 50 and upper shell 14 is twisted relative to lower shell 12, upper shell 14 and lower shell 12 are sealedly joined and cannot be pulled apart. Alternatively, lower shell 12 and upper shell 14 may be threadedly secured to each other or otherwise sealedly and releasably joined.

As can be seen, when lower shell 12 is affixed to the skin surrounding the point of entry of the gastrotomy tube and upper shell 14 is secured thereto with gastrotomy tube 11 extending through collar 38, a protective cavity 56 will be formed above and around the wound area and the axial alignment of the gastrotomy tube will be maintained. In addition, collar 38 may be secured to gastrotomy tube 11 by means of adhesive tape, thereby preventing axial displacement of gastrotomy tube 11.

As can be seen, upper shell 14 can be readily disengaged from lower shell 12 to allow visual inspection of the wound area as well as access thereto for cleaning and changing of dressings.

To improve ventilation, upper shell 14 may be furnished with plural ventilation holes 54 preferably arranged in an annular pattern. In order to prevent contamination of the wound area by dust, etc., the underside 15 of upper shell 14 is furnished with annular adhesive means and an annular thin fiber membrane 56 is adhered thereto.

Since the diameter of gastrotomy tubes may vary, it is contemplated that several upper shells will be provided with each stabilizer, each having a collar adapted to accommodate a gastrotomy tube of a different diameter. In addition, the stabilizer may be manufactured in different sizes for adults, children and infants.

What is claimed is:

1. A stabilizing apparatus for gastrotomy tubes comprising:
    a substantially cup-shaped lower shell having an upper rim and a substantially planar base provided with a central aperture adapted to permit passage of a gastrotomy tube therethrough, said aperture having a diameter substantially larger than that of the gastrotomy tube to expose an adjacent wound area, said planar base having an underside having adhesive means thereon enabling said lower shell to be removably affixed to a patient's skin,
    a substantially dome-shaped upper shell having a lower rim of substantially the same diameter as the upper rim of said lower shell, said upper shell having a body tapering upwardly and including a central opening having a collar extending upwardly therefrom, said central opening and said collar having a diameter substantially the same as that of the gastrotomy tube and adapted to receive the gastrotomy tube therethrough to maintain said gastrotomy tube in axial alignment, said upper and lower rims having cooperating interlocking means, whereby
    said upper shell may be releasably joined to said lower shell to form a protective cavity surrounding the wound area and said upper shell may be readily disengaged from said lower shell to afford visual inspection of the wound area and access thereto for cleaning and changing of dressings.

2. The stabilizing apparatus of claim 1 wherein said upper shell includes a plurality of ventilation holes and includes an underside having adhesive means thereon adapted to retain in place a thin fiber membrane underneath said holes allowing ventilation of the wound area.

3. The apparatus of claim 1 wherein said cooperating interlocking means comprises:
    an annular shelf extending inwardly from said lower rim and having teeth extending downwardly therefrom, said teeth having horizontal extensions,
    an annular ledge extending inwardly from said upper rim and having slots therein adapted to receive said teeth, whereby
    when said teeth are inserted into said slots and said upper shell is turned in the direction of said horizontal extensions, said horizontal extensions overlap said annular ledge, preventing separation of said upper shell and said lower shell.

4. The apparatus of claim 1 wherein said planar base has an upper surface having a substantially disk-shaped gauze pad resting thereon, said gauze pad having a central hole permitting passage of the gastrotomy tube therethrough, and a radial slit permitting placement and removal of said gauze pad.

* * * * *